(12) United States Patent
Neuner et al.

(10) Patent No.: US 7,022,736 B2
(45) Date of Patent: Apr. 4, 2006

(54) ENZYME INHIBITORS

(75) Inventors: Philippe Jean Sigfried Neuner, Albano Laziale (IT); Vincenzo Summa, Velletri (IT)

(73) Assignee: Istituto Di Ricerche Di Biologia Molecolare P Angeletti SpA, Pomezia (IL)

( * ) Notice: Subject to any disclaimer, the term of this patent is extended or adjusted under 35 U.S.C. 154(b) by 439 days.

(21) Appl. No.: 10/238,246

(22) Filed: Sep. 10, 2002

(65) Prior Publication Data

US 2003/0207922 A1 Nov. 6, 2003

Related U.S. Application Data

(62) Division of application No. 09/744,795, filed as application No. PCT/GB99/02446 on Jul. 27, 1999, now Pat. No. 6,492,423.

(30) Foreign Application Priority Data

Jul. 27, 1998 (GB) .................................. 9816358

(51) Int. Cl.
  *A01N 37/10* (2006.01)
  *C07C 65/32* (2006.01)
(52) U.S. Cl. .................... 514/570; 562/459; 562/463
(58) Field of Classification Search ................ 562/451, 562/463; 514/570
  See application file for complete search history.

(56) References Cited

U.S. PATENT DOCUMENTS

| | | | |
|---|---|---|---|
| 3,772,336 A | 11/1973 | Wright | |
| 3,899,508 A | 8/1975 | Wikel | |
| 4,336,397 A | 6/1982 | Cragoe, Jr. et al. | |
| 4,337,258 A | 6/1982 | Rooney et al. | |
| 4,386,092 A | 5/1983 | Oe et al. | |
| 4,423,063 A | 12/1983 | Rooney et al. | |
| 5,134,142 A | 7/1992 | Matsuo et al. | |
| 5,475,109 A | 12/1995 | Selnick et al. | |
| 5,516,797 A | 5/1996 | Armistead et al. | |
| 6,262,055 B1 | 7/2001 | Young et al. | |
| 6,306,891 B1 | 10/2001 | Selnick et al. | |
| 6,380,249 B1 | 4/2002 | Young et al. | |
| 6,620,841 B1 | 9/2003 | Fujishita et al. | |
| 6,645,956 B1 | 11/2003 | Fujishita et al. | |
| 2004/0002485 A1 | 1/2004 | Fijishita et al. | |

FOREIGN PATENT DOCUMENTS

| | | |
|---|---|---|
| DE | 3214082 A1 | 4/1981 |
| DE | 32 14082 | 10/1982 |
| EP | 0 418 845 A1 | 3/1991 |
| GB | 2 096 99 A | 10/1982 |
| JP | 61-134346 | 6/1986 |
| JP | 61-134346 A | 6/1986 |
| WO | WO 97/17316 A1 | 5/1997 |
| WO | WO 97/17317 A1 | 5/1997 |
| WO | WO 00/39086 A1 | 7/2000 |

OTHER PUBLICATIONS

Beilstein Information Service, XFIRE, XP002119720 (list of compounds and structures).
J. Tomassini et al., "Inhibition of Cap (m7GpppXm)-Dependent Endonuclease of Influenza Virus by 4-Substituted 2,4-Dioxobutanoic Acid Compounds", Antimicrob. Agents and Chemotherapy, vol. 38, No. 12, pp. 2827-2837 (Dec. 1994).
H. Zhao et al., "Arylamide Inhibitors of HIV-1 Integrase", J. Med. Chem., vol. 40, pp. 1186-1194 (1997).
H. W. R. Williams et al., "Inhibitors of Glycolic Acid Oxidase. 4-Substituted 2,4-Dioxobutanoic Acid Derivatives", J. Med. Chem., vol. 26, pp. 1196-1200 (1983).
M. Freri, "Variations in the Clasien Condensation Reaction", CA33:2488 (1938).
A. Giordani et al., "4-Phenyl-4-oxo-butanoic Acid Derivatives Inhibitors of Kynurenine 3-Hydroxylase", Bioorganic & Medicinal Chemistry Letters, vol. 8, pp. 2907-2912 (1998).
J. C. Hastings et al., "Anti-Influenza Virus Activities of 4-Substituted 2,4-Dioxobutanoic Acid Inhibitors", Antimicrob. Agents and Chem., vol. 40, No. 5, pp. 1304-1307 (May 1996).

(Continued)

*Primary Examiner*—Taofiq Solola
*Assistant Examiner*—Robert Shiao
(74) *Attorney, Agent, or Firm*—Kenneth R. Walton; Valerie J. Camara

(57) ABSTRACT

Diketoacids of Formula A are useful as inhibitors of viral polymerases. In particular hepatitis C virus RNA dependent RNA polymerase (HCV RdRp), hepatitis B virus polymerase (HBV pol) and reverse transcriptase of human immunodeficiency virus (HIV RT):

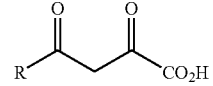

FORMULA A

The group R may be broadly chosen and is an organic moiety which contains 2 to 24 carbon atoms and includes an optionally cyclic or heterocyclic group in which the atom directly bonded to the adjacent carbonyl in the diketoacid is part of the ring structure.

20 Claims, No Drawings

OTHER PUBLICATIONS

T. T. Howarth et al., "Pyrroles and Related Compounds. Part XXVI. Pyrole Beta-Keto-esters", J. C. S. Perkin Trans. 1, vol. 4, pp. 490-501 (1974).

Derwent Abstract No. 1999-580735/49, "New indole derivatives are integrase inhibitors useful as antiviral and anti-HIV agents", abstract of WO/9950245 (Shionogi & Co., Ltd.).

Derwent Abstract No. 2000-465713, "New and known diheerocyclyl hydroxypropenone derivatives are integrase inhibitors for treating retroviral infections, including HIV and AIDS", abstract of WO 00/39086 (Shionogi & Co., Ltd.).

Y. Goldgur et al., "Structure of the HIV-1 Integrase Catalytic-Domain Complexed with an Inhibitor: A Platform for Antiviral Drug Design", Proc. Nat'l. Acad. Science USA, vol. 96, No. 23, pp. 13040-13043 (Nov. 9, 1999).

T. Munakata et al., "Pyrazole Derivatives", CA93:150250 (1980).

J. Tanaka et al., "Studies on Aromatic Sesquiterpenes. XI. Synthesis of 7-Isopropyl-3,5-dimethyl-1-naphthol", Bull. Chem. Soc. Jpn, vol. 62, No. 6, pp. 2102-2104 (1989).

A Schummer et al., "Polyfunctional (R)-2-Hydroxycarboxylic Acids and Reduction of 2-Oxo Acids with Hydrogen Gas or Formate and Resting Cells of *Proteus vulgaris*", Tetrahedron, vol. 47, No. 43, pp. 9019-9034 (1991).

B. S. Lin et al., "Substituted Pyrazolyl Compounds and Methods Employing These Compounds", CA124-202242 (1996).

R. M. Saleh, "Use of Ethyl 2-thenoylpyruvate in the Synthesis of Heterocycles and their Derivatives", CA114: 228839 (1991).

T. N. Yanborisov et al., Synthesis and Pharmacological Activity of Heteroylpyruvic Acids and Their Derivatives:, CA130:153601 (1998).

W. V. Murray et al., "A Simple Regioselective Synthesis of Ethyl 1,5-diarylpyrazole-3-carboxylates", J. Heterocyclic Chem., vol. 26, pp. 1389-1392 (1989).

D. T. Witiak et al., "Synthesis of Ethyl 6-Substituted-Chroman-and-Chromone-2-carboxylates. A Comparative Structure-Activity Study Employing the 6-Phenyl and Phenoxy Analogs in the Triton Hyperlipidemic Rate Model", J. Med. Chem., vol. 18, pp. 934-942 (1975).

Y. Andreichikov et al., "Oxalyl Derivatives of Methyl Ketones. XLIV. Synthesis of 4-aroyltetrahydro-1,5-diphenyl-2,3 poyrrolediones and Their Reaction with Amines and Hydrazine", CA107:39766g (1986).

Y. Oka et al., "Studies on the Synthesis of N-heterocyclic Compounds. XXVI. Synthesis of Pyrido[3,4-d]pyridazine Derivatives", Chem. Pharm. Bull., vol. 23, No. 10, pp. 2306-2317 (1975).

Y. Oka et al., "Studies on the Synthesis of N-heterocyclic Compounds. XXV. Syntheses of Pyrido[3,4-d]pyridazine Derivatives", Chem. Pharm. Bull., vol. 23, No. 10, pp. 2239-2250 (1975).

R. G. Cooke et al., Colouring Matters of Australian Plants. XXIII. A New Synthesis of Arylphenalenones and Naphthoxanthenones, Aust. J. Chem., vol. 33, pp. 2317-2324 (1980).

T. Seki et al., "3-Phenacyclidine-3, 4-dihydro-1H-pyrido[2,3-b]pyrazin-2-ones and 2-Phenacyclidene-1,2-dihydro-4H-pyrido-[2,3-b]pyrazine-3-ones[1]", J. Heterocyclic Chem., vol. 32, pp. 347-348 (1995).

J. G. Sweeney et al., "Total Synthesis of Apigeninidin and Luteolinidin Chlorides", Tetrahedron, vol. 37, pp. 1481-1483 (1981).

H. Burch et al., "Acylpyruvates as Potential Antifungal Agents", CA77:14833 (1972).

S. K. Biswas et al., "Mutational Analysis of the Conserved Motifs of Influenza A Virus Polymerase Basic Protein 1", J. Virology, vol. 68, No. 3, pp. 1819-1826 (1994).

K. Hara et al., "Influenza Virus RNA Polymerase PA Subunit is a Novel Serine Protease with Ser624 at the Active Site", Genes to Cells, vol. 6, pp. 87-97 (2001).

G. Kamer et al., Primary Structural Comparison of RNA-Dependent Polymerases From Plant, Animal and Bacterial Viruses, Nucleic Acids Research, vol. 12, No. 18, pp. 7269-7282 (1984).

ENZYME INHIBITORS

This application is a divisional of U.S. Ser. No. 09/744,795, filed Jan. 26, 2001, now U.S. Pat. No. 6,492,423; which is the National Stage of International Application No. PCT/GB 99/02446, filed Jul. 27, 1999, which was published in English on Feb. 10, 2000 as Published Application No. WO 00/06529; and which claims the benefit of U.S. Provisional Application No. 60/096,528, filed Aug. 13, 1998 and of British Application No. 9816358.7, filed Jul. 27, 1998.

TECHNICAL FIELD

The present invention relates to compounds useful as enzyme inhibitors, in particular as inhibitors of enzymes involved in the transfer of phosphoryl groups and, especially as inhibitors of polymerases. The invention further relates to pharmaceutical compositions containing such compounds, and to their use in the treatment of viral infections.

Polymerases are the enzymes which catalyse the formation of phosphodiester bonds in RNA and DNA. They play an essential role in viral replication and, therefore, are an important target in the fight against viral diseases such as human immunodeficiency virus (HIV), hepatitis, and poliomyelitis.

BACKGROUND ART

U.S. Pat. No. 5,475,109 describes dioxobutanoic acids substituted with piperidine or similar N-substituted saturated cycloalkyls as inhibitors of the cap-dependent endonuclease of influenza virus.

DISCLOSURE OF THE INVENTION

The present inventors have discovered that a range of diketoacids have utility as enzyme inhibitors and, in particular, as polymerase inhibitors and more particularly as inhibitors of hepatitis C NS5 RNA-dependent RNA polymerase, HBV DNA-dependent RNA polymerase and HIV DNA-dependent DNA polymerase. Their investigations indicate that these compounds may act by interfering with the binding of phosphoryl groups at the active site of the enzyme and may, therefore, have broad application in inhibiting enzymes involved in the transfer of phosphoryl groups.

According to a first aspect of the present invention there is provided a compound of formula A shown below. This compound is suitable for therapeutic use, for instance as an enzyme inhibitor.

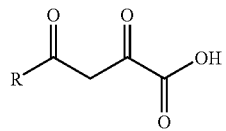

FORMULA A

Optionally, the compound may be in the form of a pharmaceutically acceptable salt or ester, which can be hydrolysed in vivo to the corresponding diketoacid.

In formula A, the group R is an organic moiety which contains from 2 to 24, preferably 4 to 20, most preferably 6 to 17 carbon atoms in total. R includes an optionally substituted cyclic or heterocyclic group in which the atom directly bonded to the adjacent carbonyl in the diketoacid is part of the ring structure. Preferably, this atom is a carbon atom.

The ring which is thus bonded to the carbonyl group is preferably a 3 to 8 membered ring, particularly a 4 to 6 membered ring.

Thus, for example, R may be selected from:

(i) optionally substituted aromatic groups, especially those including six membered rings, such as phenyl and naphthyl;

(ii) optionally substituted heteroaryl groups especially those including five and six membered rings such as thiophene, pyrrole, furan, imidazole, pyridyl, pyrimidyl, and pyridazyl; the heteroaryl ring may, optionally be fused to another ring;

(iii) optionally substituted cycloalkyl groups, especially those including five or six membered rings such as cyclopentyl, cyclohexyl and adamantyl;

(iv) optionally substituted cycloalkenyl groups, especially those including five or six numbered rings such as cyclohexenyl, cyclopentenyl;

(v) optionally substituted cyclic heteroalkyl groups, especially those including five or six numbered rings such as piperidyl, pyrrolidyl, tetrahydrofuranyl, and tetrahydropyranyl; in this class 4- piperidyl rings substituted with an aryl group at carbon 4 and on acyl or sulfonyl substituent at N1 are preferred.

In the case of optional substitution, one or more substituents may be present and a wide variety of substituents are possible. Preferred optional substituents for all compounds of the present invention are set out in the following list:

(a) —OH;

(b) —SH;

(c) -halogen, such as fluorine, chlorine or bromine, (d) —CO$_2$H;

(e) —CN;

(f) —NO2;

(g) —NR$_1$R$_2$ wherein each of R$_1$ and R$_2$ is selected from H and lower alkyl groups having 1 to 6 carbon atoms; or R$_1$ and R$_2$ together form a ring including 4 to 6 carbon atoms;

(h) —SO$_2$NR$_1$R$_2$ where R$_1$ and R$_2$ are as defined above;

(i) —CONH$_2$, —NHCO$_2$H, or —NHCOCOOH;

(j) an alkyl (or alkenyl or alkynyl group) group having 1 to 12 (2 to 12) carbon atoms, preferably 1 to 7 (2 to 7) carbon atoms optionally substituted by any one or more of the groups (a)–(i) above and/or optionally interrupted by a group selected from —O—, —S—, —NR$_3$—,

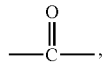

—CO$_2$—, —OCO—, —CONR$_3$—, —NR$_3$CONR$_3$—, —SO$_2$—, —NR$_3$SO$_2$—, and —SO$_2$NR$_3$—; where each R$_3$ independently is H or lower alkyl of 1 to 6 carbon atoms;

(k) an aryl or heteroaryl group having 2 to 10 carbon atoms optionally substituted with any one or more of groups (a) to (j) above;

(l) an aralkyl or heteroaralkyl group having 3 to 16 carbon atoms optionally substituted with any one or more of groups (a)–(j) above and/or in which the alkyl part of the group is optionally interrupted by a group selected from —O—, —S—, —NR$_3$—,

—CO$_2$—, —OCO—, —CONR$_3$—, —NR$_3$CONR$_3$—, —SO$_2$—, —NR$_3$SO$_2$—, and —SO$_2$NR$_3$—; where R$_3$ is as defined above;

(m)

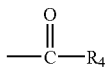

where R$_4$ is an alkyl, alkenyl, alkynyl, aryl, heteroaryl, aralkyl, or heteroaralkyl group as such groups are defined above at (j), (k) and (l);

(n)

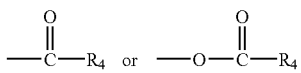

where R$_4$ is as defined above;

(o) —OR$_4$ where R$_4$ is as defined above;

(p)

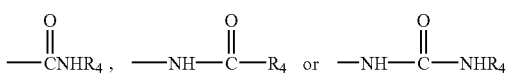

where R$_4$ is as defined above;

(q) —SO$_2$R$_4$ where R$_4$ is as defined above;

(r) —NHR$_4$ or —N(R$_4$)$_2$ where R$_4$ is as defined above;

(s) —NHSO$_2$R$_4$ or —SO$_2$NHR$_4$, where R$_4$ is as defined above;

(t) —SR$_4$ and each of optional substituents (j) to (t) above may optionally itself be substituted by one or more groups selected from (j) to (t).

A preferred class of compounds of formula A is represented by formula E:

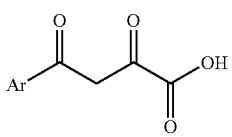

FORMULA E in which Ar is an optionally substituted aryl or heteroaryl group. Optional substituents may be selected from the list of preferred substituents set out above. Within this class of preferred compounds two especially preferred groups are set out below (formulas F and G)

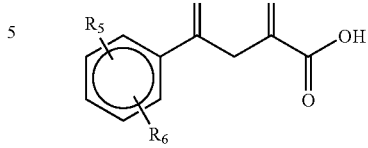

FORMULA F

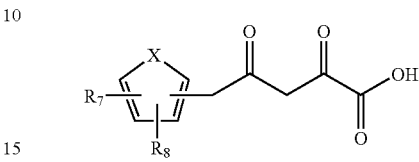

FORMULA G

R$_5$, R$_6$, R$_7$ and R$_8$ are, independently H or are selected from the optional substituents listed above and R$_7$ and R$_8$ taken together may form a 4 to 7, preferably 5 or 6 membered ring; and X is O, S, NH, or NR$_4$ where R$_4$ is as defined above.

In compounds of formula F, (which are optionally substituted phenyl diketoacids) ortho, meta and para substitution are possible.

In general, it is preferred that there is a single substituent, preferably at the position which is ortho- or meta- to the diketoacid group. Substitution at the meta-position is especially preferred. Where two substituents are present, then preferably the phenyldiketoacid is 2,5-substituted; 3,5-substitution is also possible, as is 2,4-substitution provided, in the latter case, that the substituent at the 4-position is relatively small (e.g. methyl). Disubstitution at the 2,3- and 2,6-positions is, in general, not preferred.

Preferred substituents, especially at the ortho and meta positions, are ether groups of formula (o) above (i.e. —OR$_4$), hydroxyl, and —NHSO$_2$R$_4$. It is generally preferred that no more than one substituent be —OR 4 and/or —NHSO$_2$R$_4$.

Preferred examples of —OR$_4$ groups which may be found at the ortho and meta positions and particularly at the meta position include:

—OCH$_2$Ar or, less preferably —O(CH$_2$)$_2$Ar where Ar is an optionally substituted aryl or heteroaryl group and is particularly preferably an optionally substituted phenyl group. Examples of preferred substituents on the aryl group, and especially on the phenyl ring include halogens, especially fluorine and chlorine, and electron-withdrawing groups such as —CN, —CO$_2$H, and —CF$_3$ as well as ether and aryl groups;

—O—(CH$_2$)$_3$—CN; and

—O—(CH$_2$)$_3$—C≡CH.

Preferred sulfonamide groups which may be found at the ortho- and meta-positions, particularly at the meta-position are those of formula:

—NH—SO$_2$—Ar, where Ar is an optionally substituted aryl or heteroaryl group, preferably an optionally substituted phenyl group. Preferred optional substituents for the aryl, preferably phenyl group, include: —CN; halogens, especially chlorine and fluorine, —CF$_3$, lower (C$_{1-6}$) alkyl (especially methyl), hydroxy-, ether, and —NO$_2$ groups.

For both the —OCH$_2$Ar and —NHSO$_2$Ar substituted compounds, another preferred example of Ar is naphthyl.

Other preferred substituents at the ortho and meta positions are lower (eg C$_{1-6}$) alkyl groups, especially C$_{1-4}$ alkyl, such as methyl and ethyl, but in particular methyl, aralkyl groups, especially phenylmethyl groups, optionally substituted in the phenyl ring, especially by a halogen, and nitrogen-containing substituents such as primary, secondary or tertiary amine groups, optionally in protonated form, amide, urethane, or urea groups in each of which examples there is a nitrogen atom bonded to the phenyl ring.

One particularly preferred sub class of compounds of formula F is those in which each of $R_5$ and $R_6$ is selected from H, HO—, $R_4O$—, and —$NHSO_2R_4$ provided that no more than one of $R_5$ and $R_6$ is $R_4O$— or —$NHSO_2R_4$.

In compounds of formula G the diketoacid group may be at the 2- or 3- position of the ring. In many cases substitution at the 2-position is preferred.

Preferred examples of compounds of formula G are those in which the five membered aromatic ring,

is a pyrrole or thiophene ring. In the case of the pyrrole-substituted diketoacids, the groups $R_7$ and $R_8$ may both be hydrogen and in many cases that is preferred. If $R_7$ and $R_8$ correspond to substituent groups, then these may be at any of the positions not already occupied by the diketoacid group. Examples of possible substituents include alkyl (especially methyl), halogen, and aralkyl (especially benzyl) groups.

One embodiment of pyrrole substituted diketoacid is that in which the diketoacid group is at the 2-position of the ring and where the only other substituent in the ring is on the nitrogen atom. In this case, preferred examples of the substituent $R_4$ present on the nitrogen atom, include alkyl, aryl or aralkyl groups, particularly aralkyl (such as benzyl) groups. Where an aryl or aralkyl group is present these are preferably substituted with halogen atoms, such as fluorine or chlorine, or by cyano-groups.

In the case of the thiophene-substituted diketoacids a wide range of substituents $R_7$ and $R_8$ may be employed in various positions as will be evident from the tables infra. Preferred thiophenes have an aralkyl (such as optionally substituted benzyl) or aryl (such as optionally substituted phenyl) substituent, e.g. at the 5-position of the thiophene ring.

Compounds containing furanyl rings may also be useful, especially for inhibiting HIV reverse transcriptase.

Preferred substituents are optionally substituted aryl groups (especially optionally substituted phenyl). Substitution is preferably at the 5-position of the ring.

The formulae of numerous preferred specific compounds of the present invention are presented later below.

The compounds of the present invention having formula A may be prepared by a process which comprises reaction of a compound of formula B with a dialkyloxalate of formula C followed by hydrolysis of the resulting diketo-ester of formula D:

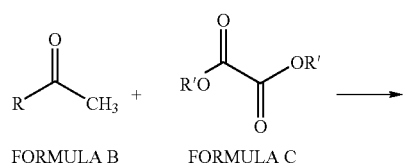

FORMULA B    FORMULA C

-continued

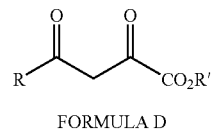

FORMULA D where R' is an alkyl group, typically having 1–6 carbon atoms. In the case where the target molecule is a pharmaceutically acceptable ester of the compound of formula A then R' in formula C may be selected accordingly, and the step of hydrolysing the compound of formula D omitted, since in vivo hydrolysis can render the compounds active.

Preferred enzymes for inhibition by the compounds of the invention are those involved in phosphate transfer, in particular polymerases such as DNA polymerases, and RNA polymerases both of which may be either RNA dependent or DNA dependant. Compounds of the invention may particularly preferably be employed in the inhibition of viral enzymes. Examples of viral enzymes include RNA-dependent RNA polymerase and reverse transcriptases.

The compounds of the invention may be used as inhibitors of plant or animal (including human) viruses.

The viruses may be RNA viruses, which may, for example, be positive single stranded viruses of which polio virus, hepatitis C virus and encephalomyocarditis are examples, negative single stranded viruses such as orthomyxoviruses, and paramyxoviruses, and retroviruses of which HIV is a prominent example. Alternatively, the viruses may be DNA viruses, especially double stranded DNA viruses such as hepatitis B virus. In particular, compounds of the present invention may inhibit one or more of the following enzymes: hepatitis C virus RNA dependent RNA polymerase (HCV RdRp), hepatitis B virus polymerase (HBV pol) and reverse transcriptase of human immunodeficiency virus (HIV RT).

Especially preferred compounds of the invention will be suitable for use as HCV RdRp inhibitors.

Other classes of enzyme involved in phosphate transfer which may be susceptible to inhibition by compounds of the present invention include phosphatases, Rnases, integrases and ribozymes.

According to a further aspect of the invention there is provided the non-therapeutic use of compound of formula A or suitable salt or ester as an enzyme inhibitor, especially as an inhibitor of polymerases, especially viral polymerases. For instance, compounds of the invention may be of utility in agriculture and horticulture for treating plants infected with or susceptible to plant virus.

According to a further aspect of the invention there is provided the use of a compound of formula A or of a pharmaceutically acceptable salt or ester thereof in the manufacture of a medicament for treatment of a viral illness in a human or animal. For instance, the medicament may be used to treat viral illness by inhibiting one or more viral polymerase. Preferably the medicament is for treatment of hepatitis, such as hepatitis B or C, particularly hepatitis C, and human immunodeficiency virus.

A still further aspect of the invention provides a pharmaceutical composition comprising a compound of formula A, or a pharmaceutically acceptable salt or ester thereof and a pharmaceutically acceptable excipient, diluent or carrier. The composition may be in any suitable form, depending on the intended method of administration. It may for example be in the form of a tablet, capsule or liquid for oral administration, or of a solution or suspension for administration parenterally.

The pharmaceutical compositions optionally also include one or more other agents for the treatment of viral infections such as an antiviral agent, or an immunomodulatory agent such as α-, β-, or γ-interferon.

A still further aspect of the invention provides a method of inhibiting an enzyme, especially a viral polymerase and/or of treating or preventing a viral illness, the method involving administering to a human or animal (preferably mammalian) subject suffering from the condition a therapeutically or prophylactically effective amount of the pharmaceutical composition described above or of a compound of formula A or salt or ester thereof. "Effective amount" means an amount sufficient to cause a benefit to the subject or at least to cause a change in the subject's condition.

The dosage rate at which the compound, salt or ester is administered will depend on the nature of the subject, the nature and severity of the condition, the administration method used, etc. Appropriate values are selectable by routine testing. The compound, salt or ester may be administered alone or in combination with other treatments, either simultaneously or sequentially. For instance, it may be administered in combination with effective amounts of antiviral agents, immunomodulators, anti-infectives, or vaccines known to those of ordinary skill in the art. It may be administered by any suitable route, including orally, intravenously, cutaneously, subcutaneously, etc. It may be administered directly to a suitable site or in a manner in which it targets a particular site, such as a certain type of cell. Suitable targeting methods are already known.

A further aspect of the invention provides a method of preparation of a pharmaceutical composition, involving admixing one or more compound of formula A or salt or ester thereof with one or more pharmaceutically acceptable adjuvants, diluents or carriers and/or with one or more other therapeutically or prophylactically active agents.

MODES FOR CARRYING OUT THE INVENTION

Embodiments of the invention are described below by the way of example only.

EXAMPLES (1) Synthesis

The synthesis of the 2,4-dioxobutanoic acids consists of a Claisen condensation reaction between a methyl ketone substrate and diethyl oxalate in the presence of sodium ethoxide in tetrahydrofuran (Scheme 1A) and the subsequent hydrolysis of the ethyl ester with sodium hydroxide in methanol (Scheme 1B)

Scheme 1A

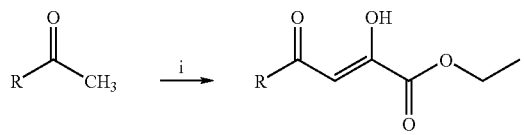

Reagents: (i) diethyl oxalate/NaOEt in THF

Scheme 1B

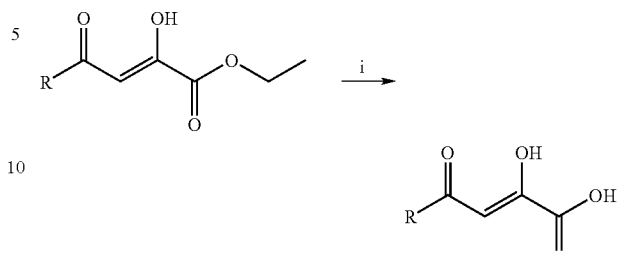

Reagents: (i) 5 eg. NaOH/MeOH

Exemplary procedure for the synthesis of the 2,4-dioxobutanoate ethyl esters (Scheme 1A)

In a 50 ml round bottom flask with a stirring bar and under an inert atmosphere, the methyl ketone compound (1.0 mmole) in 10 ml of dry tetrahydrofuran (THF) is reacted with 2 equivalents of diethyl oxalate and 2 equivalents of sodium ethoxide (NaOEt) at ambient temperature for 3 hours. When reaction is completed, the reaction mixture is poured into a 1N aqueous hydrochloric acid (HCl) and extracted with ethyl acetate (EtOAc). The organic phase is separated, washed first with water and then with brine. The organic layer is dried over sodium sulfate (Na2SO4), filtered and solvent is removed in vacuo leaving the desired dioxobutanoate ethyl ester in quantitative yield.

Exemplary Procedure for Hydrolysis of the Ethyl Ester (Scheme 1B)

In a 50 ml round bottom flask with a stirring bar, the 2,4-dioxobutanoate ethyl ester compound (1.0 mmole) in 10 ml of methanol (MeOH) is reacted with 5 equivalents of sodium hydroxide (NaOH) at ambient temperature for 2 hours.

The methanol is removed in vacuo. The aqueous residue is washed with diethyl ether (Et2O). The aqueous fraction is acidified by addition of 1N aqueous hydrochloric acid solution (HCl) and the milky mixture is extracted with two portions of ethyl acetate (EtOAc). The combined organic fractions are washed with brine. The organic layer is dried over sodium sulfate (Na2SO4), filtered and solvent is removed in vacuo leaving the desired dioxobutanoic acid product.

Using this or analogous methods, compounds were produced as set out in the following Tables, which are categorised according to their "R" group.

The Tables include IC$_{50}$ data and the methods for assay are explained after the Tables.

Notes to Table: NA=not active as an inhibitor at concentrations up to that stated.

ND=not done.

In the tables, where nitrogen atoms appear to be divalent, the presence of a hydrogen atom is implied.

TABLE I

HCV-polymerase inhibitors: examples of 2,5-substituted phenyldiketoacids

| Ex. No. | R1 | R2 | IC 50 (µM) |
|---|---|---|---|
| 1 | $X_1$—H | $X_2$—H | 5.6 |
| 2 | $X_1$—CH$_3$ | $X_2$—H | 3 |
| 3 | $X_1$—H | $X_2$—phenyl | 27.9 |
| 4 | $X_1$—H | benzyl-O—$X_2$ | 8 |
| 5 | $X_1$—H | H$_2$C=CH-CH$_2$-O—$X_2$ | 17 |
| 6 | CF$_3$—$X_1$ | $X_2$—H | 18 |
| 7 | $X_1$—H | 2,6-difluorobenzyl-O—$X_2$ | 2.92 |
| 8 | $X_1$-O-CH$_2$-phenyl | $X_2$—H | 44 |
| 9 | $X_1$-O-CH$_2$-cyclohexyl | $X_2$—H | 51 |
| 10 | $X_1$—H | cyclohexyl-CH$_2$-O—$X_2$ | 20 |

TABLE I-continued

HCV-polymerase inhibitors: examples of 2,5-substituted phenyldiketoacids

| Ex. No. | R1 | R2 | IC 50 (μM) |
|---|---|---|---|
| 11 | $X_1$—H | cyclohexyl-O—$X_2$ | 7.08 |
| 12 | $X_1$—H | benzyl-N($X_2$) | 16.7 |
| 13 | $X_1$—H | N≡C-CH$_2$CH$_2$CH$_2$-O—$X_2$ | 2.6 |
| 14 | $X_1$—H | HOOC-CH$_2$-O—$X_2$ | 26 |
| 15 | $X_1$—H | pyrrolidin-1-yl—$X_2$ | 83.5 |
| 16 | H$_2$C=CH-CH$_2$-O—$X_1$ | $X_2$—H | 4.3 |
| 17 | H$_3$C-O—$X_1$ | $X_2$—H | 11.6 |
| 18 | $X_1$—H | Ph-CH$_2$CH$_2$-O—$X_2$ | 2.2 |
| 19 | $X_1$—H | $X_2$-CH$_3$ | 11.9 |
| 20 | N≡C-CH$_2$CH$_2$CH$_2$-O—$X_1$ | $X_2$—H | 0.38 |

TABLE I-continued

HCV-polymerase inhibitors: examples of 2,5-substituted phenyldiketoacids

| Ex. No. | R1 | R2 | IC 50 (μM) |
|---|---|---|---|
| 21 | 3-cyanopropyl-O-X$_1$ | X$_2$-CH$_3$ | 0.955 |
| 22 | X$_1$-H | 2-(trifluoromethyl)benzimidazol-1-yl-butyl-O-X$_2$ | 19 |
| 23 | X$_1$-H | HO-X$_2$ | 0.94 |
| 24 | X$_1$-H | HOOC-C(O)-N(X$_2$)H | 19 |
| 25 | 4-cyanobenzyl-O-X$_1$ | X$_2$-H | 28 |
| 26 | 3-cyanobenzyl-O-X$_1$ | X$_2$-H | 26 |

TABLE I-continued

HCV-polymerase inhibitors: examples of 2,5-substituted phenyldiketoacids

| Ex. No. | R1 | R2 | IC 50 (µM) |
|---|---|---|---|
| 27 | HOOC-CH2-CH2-CH2-O-X1 | X2-H | 2.84 |
| 28 | X1-H | 3-cyanobenzyl-O-X2 | 6.2 |
| 29 | H3C-CH2-O-X1 | X2-H | 3.9 |
| 30 | X1-H | H3C-(CH2)4-O-X2 | 15 |
| 31 | H3C-(CH2)6-O-X1 | X2-H | 18 |
| 32 | (H3C)2CH-CH2-O-X1 | X2-H | 6.1 |

TABLE I-continued

HCV-polymerase inhibitors: examples of 2,5-substituted phenyldiketoacids

| Ex. No. | R1 | R2 | IC 50 (μM) |
|---|---|---|---|
| 33 | cyclohexyl-S-X₁ | X₂-H | 18.2 |
| 34 | H₃C-CH₂-CH₂-S-X₁ | X₂-H | 9.6 |
| 35 | N≡C-CH₂CH₂CH₂-O-X₁ | X₂-O-CH₂CH₂CH₂-C≡N | 6.1 |
| 36 | N≡C-CH₂CH₂CH₂-O-X₁ | X₂-Cl | 1.6 |
| 37 | 4-F-C₆H₄-O-X₁ | X₂-H | 18 |
| 38 | 4-Cl-C₆H₄-O-X₁ | X₂-H | 16 |
| 39 | 4-H₃C-C₆H₄-O-X₁ | X₂-H | 22 |

TABLE I-continued

HCV-polymerase inhibitors: examples of 2,5-substituted phenyldiketoacids

| Ex. No. | R1 | R2 | IC 50 (μM) |
|---|---|---|---|
| 40 | 4-fluorobenzyl-$X_1$ | $X_2$-H | 8.3 |
| 41 | $X_1$-H | N,N-dibenzylamino-$X_2$ | 28.9 |
| 42 | N,N-dibenzylamino-$X_2$ | $X_2$-H | 16.6 |
| 43 | $X_1$-H | 3-chlorobenzyl-$X_2$ | 20 |
| 44 | $X_1$-H | phenoxy-$X_2$ | 18.5 |
| 45 | $X_1$-H | 4-chlorobenzyl-$X_2$ | 12.9 |
| 46 | $X_1$-H | 4-fluorobenzyl-$X_2$ | 30.1 |
| 47 | $X_1$-H | 3,4-dihydronaphthalen-1-yl-$X_2$ | 20.7 |
| 48 | $X_1$-H | 3-bromobenzyl-$X_2$ | 22 |

TABLE I-continued

HCV-polymerase inhibitors: examples of 2,5-substituted phenyldiketoacids

| Ex. No. | R1 | R2 | IC 50 (μM) |
|---|---|---|---|
| 49 | X₁—H | 3,5-dibromobenzyl-X₂ | 32 |
| 50 | N≡C-(CH₂)₃-O-X₁ | X₂—H | 7.8 |
| 51 | HC≡C-(CH₂)₃-O-X₁ | X₂—H | 1.9 |
| 52 | CH₃-(CH₂)₃-O-X₁ | X₂—H | 10 |
| 53 | N≡C-(CH₂)₃-O-X₁ | X₂—OH | 0.115 |
| 54 | N≡C-(CH₂)₃-O-X₁ | X₂—Br | 2.3 |

TABLE I-continued

HCV-polymerase inhibitors: examples of 2,5-substituted phenyldiketoacids

| Ex. No. | R1 | R2 | IC 50 (μM) |
|---|---|---|---|
| 55 | (E)-styryl-X$_1$ | X$_2$-H | 10.8 |
| 56 | N≡C-(CH$_2$)$_3$-O-X$_1$ | Cl-(CH$_2$)$_3$-C≡C-X$_2$ | 23.6 |
| 57 | N≡C-(CH$_2$)$_3$-O-X$_1$ | (E)-styryl-X$_2$ | 2.1 |
| 58 | N≡C-(CH$_2$)$_3$-O-X$_1$ | phenyl-X$_2$ | 13.6 |
| 59 | X$_1$-O-(CH$_2$)$_4$-CH$_3$ | X$_2$-H | 25.3 |
| 60 | X$_1$-H | H$_3$C-O-X$_2$ | 40 |

TABLE I-continued

HCV-polymerase inhibitors: examples of 2,5-substituted phenyldiketoacids

| Ex. No. | R1 | R2 | IC 50 (µM) |
|---|---|---|---|
| 61 | X$_1$—H | NHX$_2$, Boc (tert-butoxycarbonylamino) | 31 |
| 62 | X$_1$—H | H$_2$N—X$_2$ | 10 |
| 63 | X$_1$—O—CH$_2$CH$_2$CH$_2$—CN | H$_3$N$^+$—X$_2$ | 1.7 |
| 64 | X$_1$—H | 2-cyanobenzyl-O—X$_2$ | 0.23 |
| 65 | X$_1$—O—CH$_2$-(2-cyanophenyl) | X$_2$—H | 45 |
| 66 | X$_1$—H | X$_2$—NH—C(O)—phenyl | 11 |
| 67 | X$_1$—H | X$_2$—NH—S(O)$_2$—phenyl | 16 |

TABLE I-continued

HCV-polymerase inhibitors: examples of 2,5-substituted phenyldiketoacids

| Ex. No. | R1 | R2 | IC 50 (µM) |
|---|---|---|---|
| 68 | X₁—H | X₂—NH—C(=O)—(4-cyanophenyl) | 30 |
| 69 | X₁—O—CH₂CH₂—C(CN)(phenyl)₂ | X₂—H | 14 |
| 70 | X₁—H | X₂—NH—C(=O)—(3-cyanophenyl) | 9.2 |
| 71 | X₁—H | X₂—O—CH₂—(pyridin-3-yl) | 10.6 |
| 72 | X₁—H | X₂—NH—S(=O)₂—(2-cyanophenyl) | 0.48 |

TABLE I-continued

HCV-polymerase inhibitors: examples of 2,5-substituted phenyldiketoacids

| Ex. No. | R1 | R2 | IC 50 (μM) |
|---|---|---|---|
| 73 | X₁—H | X₂—O—CH₂-(2-pyridyl) | 5.6 |
| 74 | X₁—H | X₂—NH—SO₂-(4-cyanophenyl) | 3.6 |
| 75 | X₁—H | X₂—NH—SO₂—CH₃ | 19.2 |
| 76 | X₁—H | X₁—O—CH₂-(3-pyridyl) | 50 |
| 77 | X₁—H | X₂—NH—SO₂-(2-bromophenyl) | 4.8 |
| 78 | X₁—H | X₂—NH—SO₂-(1-naphthyl) | 0.67 |

TABLE I-continued

HCV-polymerase inhibitors: examples of 2,5-substituted phenyldiketoacids

| Ex. No. | R1 | R2 | IC 50 (µM) |
|---|---|---|---|
| 79 | X₁–H | X₂–N(H)–CH₂–(3-carboxyphenyl) | 6 |
| 80 | X₁–H | X₂–N(H)–C(=O)–NH–phenyl | 3 |
| 81 | X₁–H | X₂–N(H)–C(=O)–O–CH₂–phenyl | 1.4 |
| 82 | X₁–H | X₂–O–CH₂–(thiophene-2-carboxylic acid tert-butyl ester, 3-substituted) | 19 |
| 83 | X₁–H | X₂–O–CH₂–CH=CH–phenyl (trans-cinnamyl) | 9.4 |

TABLE I-continued

HCV-polymerase inhibitors: examples of 2,5-substituted phenyldiketoacids

| Ex. No. | R1 | R2 | IC 50 (μM) |
|---|---|---|---|
| 84 | $X_1$–H | $X_2$–O–CH$_2$–(3-(2-carboxy)thiophene) | 0.95 |
| 85 | $X_1$–H | $X_2$–N(H)–C(O)–(2-chlorophenyl) | 13 |
| 86 | $X_1$–H | $X_2$–O–CH$_2$–(2-fluoro-3-methylphenyl) | 2.05 |
| 87 | $X_1$–H | $X_2$–O–CH$_2$–(2-chloro-4-fluorophenyl) | 2.3 |
| 88 | $X_1$–H | $X_2$–N(H)–SO$_2$–(2,5-dichlorophenyl) | 0.7 |

TABLE I-continued

HCV-polymerase inhibitors: examples of 2,5-substituted phenyldiketoacids

| Ex. No. | R1 | R2 | IC 50 (μM) |
|---|---|---|---|
| 89 | $X_1$-H | $X_2$-O-CH$_2$-(2-Br-phenyl) | 3.3 |
| 90 | $X_1$-H | $X_2$-O-CH$_2$-(2-COOH-phenyl) | 1.8 |
| 91 | $X_1$-H | $X_2$-O-CH$_2$-(2-CH$_3$-phenyl) | 6.2 |
| 92 | $X_1$-H | $X_2$-O-CH$_2$-(3-OCH$_3$-phenyl) | 1 |
| 93 | $X_1$-H | $X_2$-O-CH$_2$-(3-CF$_3$-phenyl) | 1.9 |

TABLE I-continued

HCV-polymerase inhibitors: examples of 2,5-substituted phenyldiketoacids

| Ex. No. | R1 | R2 | IC 50 (μM) |
|---|---|---|---|
| 94 | X₁–H | X₂–O–CH₂–(3-fluorophenyl) | 5.8 |
| 95 | X₁–H | X₂–NH–SO₂–(2,5-dichlorothiophen-3-yl) | 0.48 |
| 96 | X₁–H | X₂–O–CH₂–(4-phenylphenyl) | 50 |
| 97 | X₁–H | X₂–O–CH₂–(2-phenylphenyl) | 2.8 |
| 98 | X₁–H | X₂–O–CH₂–(4-chloro-3-(... )-5-carboxyphenyl) | 1 |

TABLE I-continued

HCV-polymerase inhibitors: examples of 2,5-substituted phenyldiketoacids

| Ex. No. | R1 | R2 | IC 50 (µM) |
|---|---|---|---|
| 99 | X₁—H | X₂—O—CH₂—(2-cyano-4-fluorophenyl) | 0.6 |
| 100 | X₁—H | X₂—O—CH₂—(3-chloro-4-carboxyphenyl) | 7.8 |
| 101 | X₁—H | X₂—N(H)—SO₂—(thiophen-2-yl) | 7 |
| 102 | X₁—H | X₂—N(H)—SO₂—(5-chlorothiophen-2-yl) | 1.5 |
| 103 | X₁—H | X₂—O—CH₂—(5-phenylisoxazol-3-yl) | 6 |

TABLE I-continued

HCV-polymerase inhibitors: examples of 2,5-substituted phenyldiketoacids

| Ex. No. | R1 | R2 | IC 50 (μM) |
|---|---|---|---|
| 104 | X1—H | 3-phenoxybenzyl ether (X2—O—CH2—C6H4—O—C6H5) | 50 |
| 105 | X1—H | pyridine N-oxide-2-yl-methyl ether (X2—O—CH2-(2-pyridyl N-oxide)) | 13.7 |
| 106 | X1—H | (5-methylisoxazol-3-yl)methyl ether (X2—O—CH2-(5-methylisoxazol-3-yl)) | 6.8 |
| 107 | X1—H | (3-chloro-2-cyanophenyl)methyl ether (X2—O—CH2-(3-chloro-2-cyanophenyl)) | 0.14 |
| 108 | X1—H | benzylsulfonamide (X2—N(H)—S(O)2—CH2—C6H5) | 6.9 |

TABLE I-continued
HCV-polymerase inhibitors: examples of 2,5-substituted phenyldiketoacids
| Ex. No. | R1 | R2 | IC 50 (µM) |
|---|---|---|---|
| 109 | 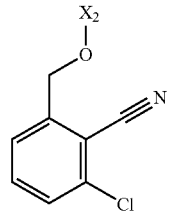 |  | 0.17 |
| 110 | 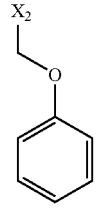 |  | 30 |
| 111 | 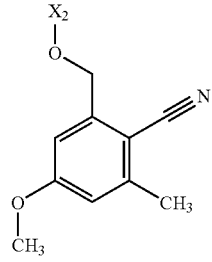 |  | 0.12 |
| 112 | 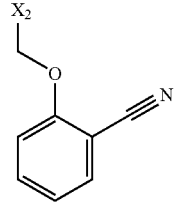 |  | 1.33 |
| 113 | 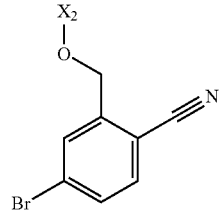 | | 0.1 |

TABLE I-continued

HCV-polymerase inhibitors: examples of 2,5-substituted phenyldiketoacids

| Ex. No. | R1 | R2 | IC 50 (μM) |
|---|---|---|---|
| 114 | X₁—H | naphthalen-2-ylsulfonyl-N(X₂) | 0.5 |
| 115 | X₁—H | 2-chloro-4-(trifluoromethyl)phenylsulfonyl-N(X₂) | 3.7 |
| 116 | X₁—H | 4-cyano-3-(X₂-oxymethyl)biphenyl | 0.3 |
| 117 | X₁—H | 3,5-dichlorophenylsulfonyl-N(X₂) | 0.14 |
| 118 | X₁—H | 2,3-dichlorophenylsulfonyl-N(X₂) | 0.2 |

TABLE I-continued

HCV-polymerase inhibitors: examples of 2,5-substituted phenyldiketoacids

| Ex. No. | R1 | R2 | IC 50 (μM) |
|---|---|---|---|
| 119 | X₁—H | 2,4,5-trichlorophenyl-SO₂-N(X₂)- | 0.049 |
| 120 | X₁—H | 2,6-dichlorophenyl-SO₂-N(X₂)- | 0.36 |
| 121 | X₁—H | phenethyl-NH-C(O)-N(X₂)- | 4 |
| 122 | X₁—H | 2-cyano-3-methylphenyl-CH(CH₃)-O-X₂ | 2 |
| 123 | X₁—H | 2-methyl-3-chlorophenyl-SO₂-N(X₂)- | 0.29 |

TABLE I-continued

HCV-polymerase inhibitors: examples of 2,5-substituted phenyldiketoacids

| Ex. No. | R1 | R2 | IC 50 (μM) |
| --- | --- | --- | --- |
| 124 | $X_1$—H | $X_2$—NH—SO$_2$—(4-biphenyl) | 28 |
| 125 | $X_1$—H | $X_2$—NH—SO$_2$—(2,3,4-trichlorophenyl) | 0.17 |
| 126 | $X_1$—H | $X_2$—O—CH$_2$—(2-cyano-3,5-dichlorophenyl) | 0.056 |
| 127 | $X_1$—H | $X_2$—NH—SO$_2$—(3,5-dichloro-2-hydroxyphenyl) | 0.3 |
| 128 | $X_1$—H | $X_2$—NH—SO$_2$—(2-ethoxycarbonylphenyl) | 24 |

TABLE I-continued

HCV-polymerase inhibitors: examples of 2,5-substituted phenyldiketoacids

| Ex. No. | R1 | R2 | IC 50 (μM) |
|---|---|---|---|
| 129 | $X_1$-H | 5-chloro-2-methoxyphenylsulfonamide ($X_2$-NH-SO$_2$-Ar) | 1.6 |
| 130 | $X_1$-H | 4-bromo-2,5-dichlorothiophene-3-sulfonamide ($X_2$-NH-SO$_2$-Ar) | 0.14 |
| 131 | $X_1$-H | 3-chlorophenylsulfonamide ($X_2$-NH-SO$_2$-Ar) | 0.78 |
| 132 | $X_1$-H | naphthalen-1-ylmethoxy ($X_2$-O-CH$_2$-Ar) | 0.67 |
| 133 | $X_1$-H | 3,4-dichlorobenzyloxy ($X_2$-O-CH$_2$-Ar) | 3.2 |

TABLE I-continued

HCV-polymerase inhibitors: examples of 2,5-substituted phenyldiketoacids

| Ex. No. | R1 | R2 | IC 50 (μM) |
|---|---|---|---|
| 134 | $X_1$—H | $X_2$—N(H)—SO$_2$—CH$_2$CH$_2$CH$_2$Cl | 23 |
| 135 | $X_1$—H | $X_2$—N(H)—SO$_2$—(3,5-dichloro-4-(2-chloro-4-nitrophenoxy)phenyl) | 21 |
| 136 | $X_1$—H | $X_2$—N(H)—SO$_2$—(3,4-dichlorophenyl) | 0.2 |
| 137 | $X_1$—H | $X_2$—N(H)—SO$_2$—(3-chloro-4-methylphenyl) | 0.9 |

TABLE I-continued

HCV-polymerase inhibitors: examples of 2,5-substituted phenyldiketoacids

| Ex. No. | R1 | R2 | IC 50 (µM) |
|---------|----|----|------------|
| 138 | X1—H | X2—N(H)—S(O)2—(2-Cl,4-F-phenyl) | 1.1 |
| 139 | X1—H | X2—O—CH2—(2,6-diCl-phenyl) | 1.4 |
| 140 | X1—H | X2—N(H)—S(O)2—(2,6-diCl,4-CF3-phenyl) | 1 |
| 141 | X1—H | X2—N(H)—S(O)2—(4-Cl,3-NO2-phenyl) | 0.56 |
| 142 | X1—H | X2—N(H)—S(O)2—(3-NO2-phenyl) | 0.4 |

TABLE I-continued

HCV-polymerase inhibitors: examples of 2,5-substituted phenyldiketoacids

| Ex. No. | R1 | R2 | IC 50 (μM) |
|---|---|---|---|
| 143 | X$_1$—H | N(X$_2$)-SO$_2$-(3-Cl,4-F-phenyl) | 0.45 |
| 144 | X$_1$—H | SO$_2$-NH-phenyl | 14 |
| 145 | X$_1$—H | SO$_2$-NH-(4-Cl-phenyl) | 1.2 |
| 146 | X$_1$—H | N(X$_2$)-SO$_2$-(2,4,6-triMe-phenyl) | 15 |
| 147 | X$_1$—H | N(X$_2$)-SO$_2$-(2,5-diMe-4-Cl-phenyl) | 1.3 |

TABLE I-continued

HCV-polymerase inhibitors: examples of 2,5-substituted phenyldiketoacids

| Ex. No. | R1 | R2 | IC 50 (μM) |
|---|---|---|---|
| 148 | X₁—H | N(X₂)-SO₂-(2,4,6-trichlorophenyl) | 0.26 |
| 149 | X₁—H | N(X₂)-SO₂-(2,4-dichloro-5-methylphenyl) | 0.55 |
| 150 | X₁—H | N(X₂)-SO₂-(2,4-dichloro-6-methylphenyl) | 2.3 |
| 151 | X₁—H | N(X₂)-SO₂-(2,4-dichlorophenyl) | 0.5 |
| 152 | X₁—F | X₂-CH₂-phenyl | 20 |

TABLE I-continued

HCV-polymerase inhibitors: examples of 2,5-substituted phenyldiketoacids

| Ex. No. | R1 | R2 | IC 50 (μM) |
|---|---|---|---|
| 153 | X₁–H | 2H-benzotriazol-2-ylmethyl-X₂ | 19 |
| 154 | X₁–H | 1H-benzotriazol-1-ylmethyl-X₂ | 30 |

TABLE II

HCV-polymerase inhibitors: examples of 3,5-substituted phenyldiketoacids

| Ex. No. | R1 | R2 | IC 50 (μM) |
|---|---|---|---|
| 155 | X₁–OH | benzyl-O-X₂ | 1.4 |
| 156 | HO–X₁ | X₂–OH | 1.3 |
| 157 | N≡C–(CH₂)₃–O–X₁ | X₂–OH | 0.9 |
| 158 | HO–X₁ | X₂–O–CH₂–(2-cyanophenyl) | 0.2 |

TABLE II-continued

HCV-polymerase inhibitors: examples of 3,5-substituted phenyldiketoacids

[Structure: 3,5-disubstituted phenyl ring with R1 and R2 substituents attached to a -C(O)-CH=C(OH)-C(O)OH diketoacid side chain]

| Ex. No. | R1 | R2 | IC 50 (µM) |
|---|---|---|---|
| 159 | CH₃-O-X₁ (methoxy) | benzofuran-2-yl-CH₂-X₂ | 20 |
| 160 | HO-X₁ | 3-chloro-2-cyanophenyl-CH₂-O-CH₂-X₂ | 0.1 |

TABLE III

HCV-polymerase inhibitors: examples of 2,4-substituted phenyldiketoacids

[Structure: 2,4-disubstituted phenyl ring with R1 and R2 substituents attached to a -C(O)-CH=C(OH)-C(O)OH diketoacid side chain]

| Ex. No. | R1 | R2 | IC 50 (µM) |
|---|---|---|---|
| 161 | H-X₁ | H₃C-X₂ | 2.8 |
| 162 | H-X₁ | HO-X₂ | 5.5 |
| 163 | H-X₁ | F-X₂ | 26 |
| 164 | H-X₁ | H₃C-CH₂-X₂ | 47 |
| 165 | CH₃-X₁ | H₃C-X₂ | 2 |
| 166 | H-X₁ | Cl-X₂ | 20 |
| 167 | N≡C-CH₂-CH₂-CH₂-O-X₁ | H₃C-X₂ | 0.6 |

TABLE IV

HCV-polymerase inhibitors: examples of 2,3-substituted phenyldiketoacids

| Ex. No. | R1 | R2 | IC 50 (μM) |
|---|---|---|---|
| 168 | NC-(CH2)3-O-X1 | CH2=CH-CH2-X2 | 18 |
| 169 | CH3-X1 | PhCH2-X2 | >50 |
| 170 | Ph-CH(X2)-(CH2)3-X1 | H-X2 | >50 |

TABLE V

HCV-polymerase inhibitors: examples of 2,6-substituted phenyldiketoacids

| Ex. No. | R1 | R2 | IC 50 (μM) |
|---|---|---|---|
| 171 | NC-(CH2)3-O-X1 | X2-O-(CH2)3-CN | 12 |
| 172 | X1-O-CH3 | H3C-O-X2 | >50 |

TABLE VIa

HCV-polymerase inhibitors: examples of pyrrole-2-substituted diketoacids

| Ex. No. | R1 | IC 50 (μM) |
|---|---|---|
| 173 | N-(4-cyanobutyl)-pyrrol-2-yl-X1 | 21 |
| 174 | N-(5-cyanopentyl)-pyrrol-2-yl-X1 | 13.4 |
| 175 | N-(cyclopentylmethyl)-pyrrol-2-yl-X1 | 25 |
| 176 | N-benzyl-pyrrol-2-yl-X1 | 29 |
| 177 | N-(4-fluorophenyl)-pyrrol-2-yl-X1 | 25 |
| 178 | N-(cyclohexylmethyl)-pyrrol-2-yl-X1 | 17.9 |

TABLE VIa-continued
HCV-polymerase inhibitors: examples of pyrrole-2-substituted diketoacids
| Ex. No. | R1 | IC 50 (μM) |
|---|---|---|
| 179 | 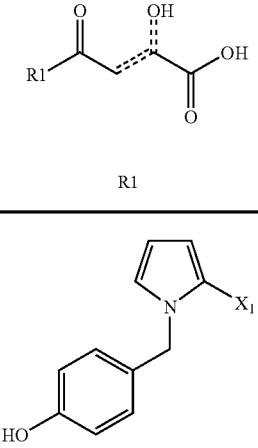 | 12.8 |
| 180 | 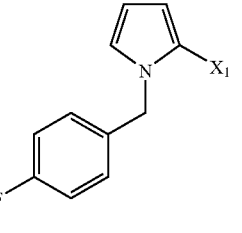 | 93 |
| 181 | 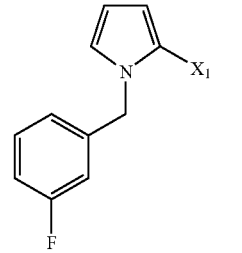 | 30 |
| 182 | 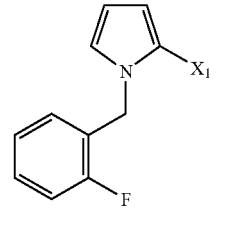 | 30 |
| 183 | 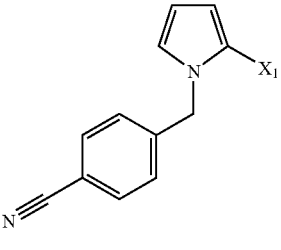 | 32 |
| 184 | 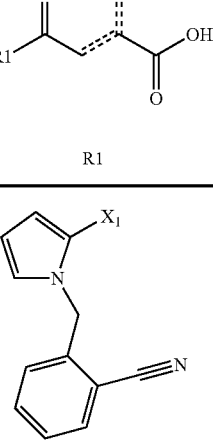 | 6.7 |
| 185 | 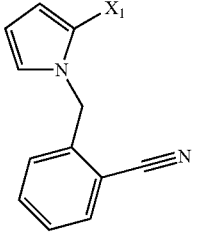 | 6.3 |
| 186 | 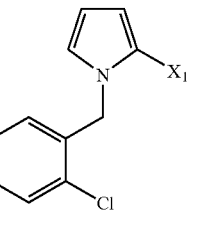 | 24 |
| 187 | 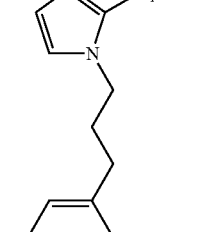 | 36 |
| 188 | 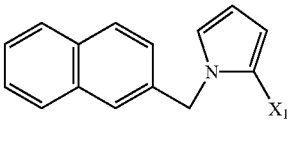 | 12.7 |

TABLE VIa-continued
HCV-polymerase inhibitors: examples of pyrrole-2-substituted diketoacids
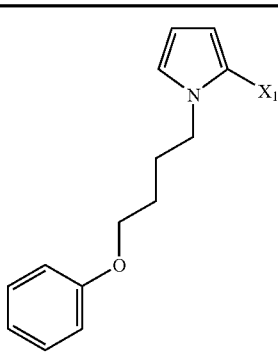
| Ex. No. | R1 | IC 50 (µM) |
|---|---|---|
| 189 | 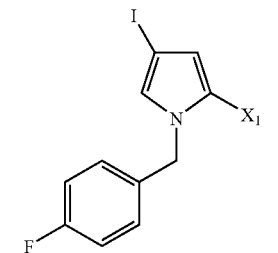 | 28 |
| 190 | 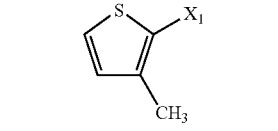 | 18 |
| 191 | 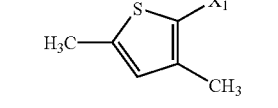 | 10 |
| 192 | 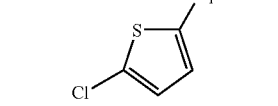 | 8.2 |
| 193 | 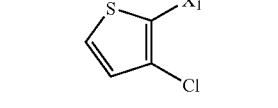 | 12 |
| 194 | 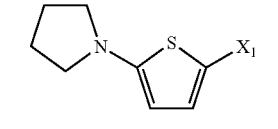 | 16 |
| 195 | 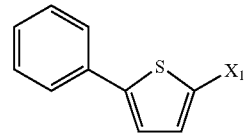 | 11.1 |
TABLE VIa-continued
HCV-polymerase inhibitors: examples of pyrrole-2-substituted diketoacids
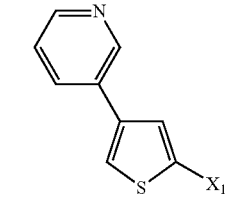
| Ex. No. | R1 | IC 50 (µM) |
|---|---|---|
| 196 | 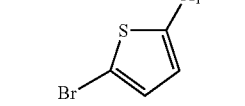 | 15 |
| 197 | 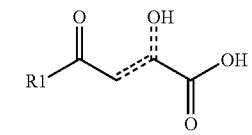 | 11 |
| 198 | 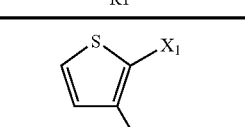 | 7.9 |
TABLE VIb
HCV-polymerase inhibitors: examples of thiophene-2-substituted diketoacids
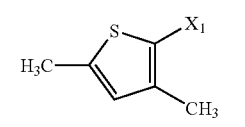
| Ex. No. | R1 | IC 50 (µM) |
|---|---|---|
| 191 | 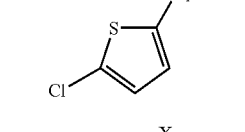 | 10 |
| 192 | 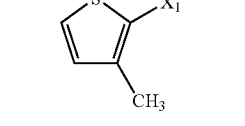 | 8.2 |
| 193 | 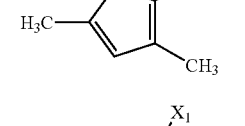 | 12 |
| 194 | 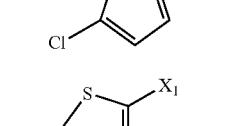 | 16 |

TABLE VIb-continued

HCV-polymerase inhibitors: examples of thiophene-2-substituted diketoacids

| Ex. No. | R1 | IC 50 (μM) |
|---|---|---|
| 195 | pyrrolidinyl-thiophene-X₁ | 11.1 |
| 196 | phenyl-thiophene-X₁ | 15 |
| 197 | pyridin-3-yl-thiophene-X₁ | 11 |
| 198 | 5-bromothiophene-X₁ | 7.9 |
| 199 | 3-bromothiophene-X₁ | 17 |
| 200 | piperidinyl-thiophene-X₁ | 8.2 |
| 201 | 3,4-dimethylthieno[thiophene]-X₁ | 20 |
| 202 | benzyl-thiophene-X₁ | 68 |
| 203 | diallylamino-thiophene-X₁ | 19.8 |
| 204 | 4,5-dihydronaphtho[2,1-b]thiophene-X₁ | 11 |
| 205 | (3-fluorobenzyl)-thiophene-X₁ | 74 |
| 206 | (4-fluorobenzyl)-thiophene-X₁ | 65 |
| 207 | 3-(3-fluorobenzyl)-thiophene-X₁ | 9.9 |
| 208 | 3-(4-fluorobenzyl)-thiophene-X₁ | 11.6 |
| 209 | 3-(phenylthio)-thiophene-X₁ | 12.6 |
| 210 | 8-fluoro-4H-thiochromeno[fused]-X₁ | 27 |

TABLE VIb-continued

HCV-polymerase inhibitors: examples of thiophene-2-substituted diketoacids

| Ex. No. | R1 | IC 50 (μM) |
|---|---|---|
| 211 | 3-chlorobenzyl-thiophen-2-yl | 82 |
| 212 | 3-(3-chlorobenzyl)thiophen-2-yl | 7.5 |
| 213 | 3-(3-fluorophenylthio)thiophen-2-yl | 5.9 |
| 214 | 4-phenyl-4,5,6,7-tetrahydrobenzothiophen-2-yl | 17 |
| 215 | 2-(3,4-dihydroisoquinolin-2(1H)-yl)thiophen-5-yl | 15.3 |

TABLE VIc

HCV-polymerase inhibitors: examples of furan-2-substituted diketoacids

| Ex. | R1 | IC 50 (μM) |
|---|---|---|
| 216 | furan-2-yl | 50 |
| 217 | 5-methylfuran-2-yl | 58 |
| 218 | 5-(3-chloro-4-fluorophenyl)furan-2-yl | 41.2 |

TABLE VIIa

HCV-polymerase inhibitors: examples of pyrrole-3-substituted diketoacids

| Ex. No. | R1 | IC 50 (μM) |
|---|---|---|
| 219 | 2,4-dimethyl-1H-pyrrol-3-yl | 23.7 |
| 220 | 1-(3-cyanobenzyl)-1H-pyrrol-3-yl | 4.6 |
| 221 | 2-(3-fluorobenzyl)-1-methyl-1H-pyrrol-4-yl | 20.6 |

TABLE VIIb

HCV-polymerase inhibitors: examples of thiophene-3-substituted diketoacids

| Ex. No. | R1 | IC 50 (μM) |
|---|---|---|
| 222 | 3-thienyl | 4 |
| 223 | 2,5-dimethylthiophen-3-yl | 27 |
| 224 | 2,5-dichlorothiophen-3-yl | 50 |
| 225 | 2-methyl-5-phenylthiophen-3-yl | 167 |
| 226 | 2-(4-methylphenyl)thiophen-3-yl | 17 |
| 227 | 2-(thiophen-2-ylmethyl)thiophen-3-yl | 15 |
| 228 | 2-(4-fluorobenzyl)thiophen-3-yl | 17.8 |
| 229 | 2-(3-fluorobenzyl)thiophen-3-yl | 80 |
| 230 | 2-(2-fluorobenzyl)thiophen-3-yl | 8.6 |
| 231 | 2-(4-chlorobenzyl)thiophen-3-yl | 9.4 |
| 232 | 2-(3-chlorobenzyl)thiophen-3-yl | 11.8 |
| 233 | 2-(2-chlorobenzyl)thiophen-3-yl | 9.2 |
| 234 | 2-((4-fluorophenyl)thio)thiophen-3-yl | 14.5 |

TABLE VIIb-continued

HCV-polymerase inhibitors: examples of thiophene-3-substituted diketoacids

| Ex. No. | R1 | IC 50 (μM) |
|---|---|---|
| 235 | 3-chlorophenylthio-thiophen-2-yl (X₁ at 3-position) | 7.5 |
| 236 | benzothiophen-3-yl (X₁) | 26 |

TABLE VIIc

HCV-polymerase inhibitors: examples of furan-3-substituted diketoacids

| Ex. No. | R1 | IC 50 (μM) |
|---|---|---|
| 237 | 2,5-dimethylfuran-3-yl (X₁) | 14 |
| 238 | 2,4-dimethylfuran-3-yl (X₁) | 47.5 |

TABLE VIII

HCV-polymerase inhibitors: examples of alkyl-diketoacids

| Ex. No. | R1 | IC 50 (μM) |
|---|---|---|
| 239 | 1-methylcyclopropyl (X₁) | 9.4 |
| 240 | isopropyl (X₁) | 18 |
| 241 | tert-butyl (X₁) | 37 |
| 242 | 4-methylcyclohex-3-enyl (X₁) | 12.8 |
| 243 | adamantyl (X₁) | 6.7 |
| 244 | diphenylmethyl (X₁) | 77 |
| 245 | 1-(butylsulfonyl)-3-(4-chlorobenzyl)piperidin-3-yl (X₁) | 81.4 |

TABLE VIII-continued

HCV-polymerase inhibitors: examples of alkyl-diketoacids

| Ex. No. | R1 | IC 50 (µM) |
|---|---|---|
| 246 | 1-(3-chlorophenylsulfonyl)-4-phenylpiperidin-4-yl | 18 |
| 247 | 1-benzyl-3-(4-chlorobenzyl)piperidinium-3-yl | 45 |
| 248 | 1-(quinolin-8-ylsulfonyl)-4-phenylpiperidin-4-yl | 10 |
| 249 | 1-(N,N-diphenylcarbamoyl)-4-phenylpiperidin-4-yl | 60 |
| 250 | 1-(3,4-dichlorophenylsulfonyl)-4-phenylpiperidin-4-yl | 17 |
| 251 | 1-(2,4,5-trichlorophenylsulfonyl)-4-phenylpiperidin-4-yl | 21 |
| 252 | 1-(4-bromophenylsulfonyl)-3-(4-chlorobenzyl)piperidin-3-yl | 61 |
| 253 | 1-(5-dimethylaminonaphthalen-1-ylsulfonyl)-3-(4-chlorobenzyl)piperidin-3-yl | 55 |
| 254 | cyclohex-1-en-1-yl | 14 |
| 255 | 2-methylcyclopent-1-en-1-yl | 16.7 |
| 256 | cyclohexyl | 25 |

TABLE VIII-continued
HCV-polymerase inhibitors: examples of alkyl-diketoacids
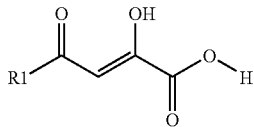
| Ex. No. | R1 | IC 50 (μM) |
|---|---|---|
| 257 | 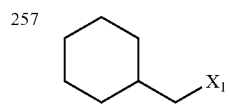 | 50 |
TABLE IXa
most active HCV-inhibitors
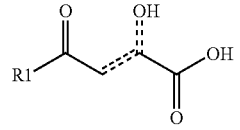
| Ex. No. | R1 | HCV | HIV | HBV |
|---|---|---|---|---|
| 126 | 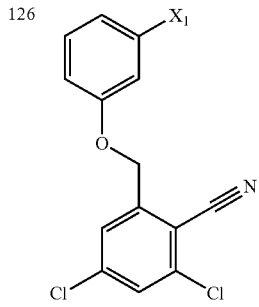 | 0.056 | 100 | ND |
| 160 | 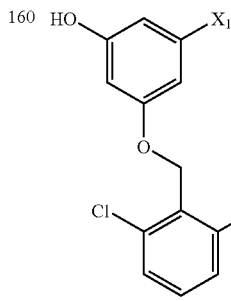 | 0.1 | NA | ND |
| 113 | 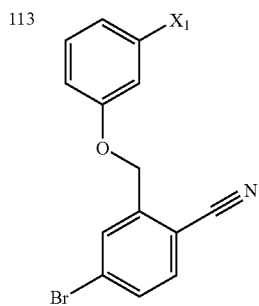 | 0.1 | 90 | ND |
TABLE IXa-continued
most active HCV-inhibitors
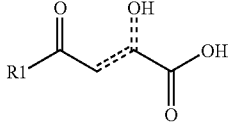
| Ex. No. | R1 | HCV | HIV | HBV |
|---|---|---|---|---|
| 53 | 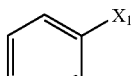 | 0.115 | 37 | ND |
| 111 | 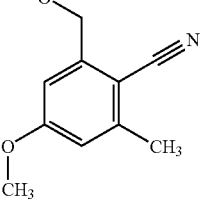 | 0.12 | 80 | ND |
| 107 | 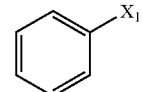 | 0.14 | 58 | ND |
| 117 | 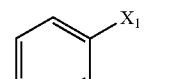 | 0.14 | 100 | ND |

TABLE IXa-continued
most active HCV-inhibitors
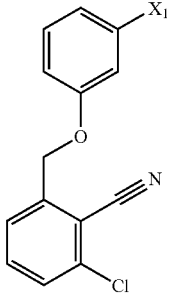
| Ex. No. | R1 | HCV | HIV | HBV |
|---|---|---|---|---|
| 109 | 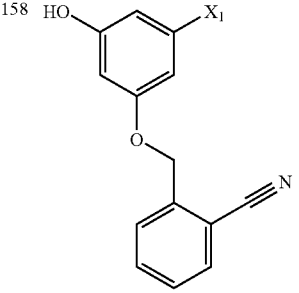 | 0.17 | NA | ND |
| 158 | 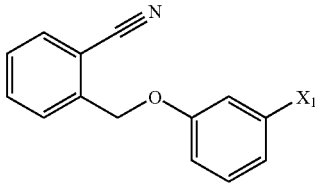 | 0.2 | NA | ND |
| 64 | 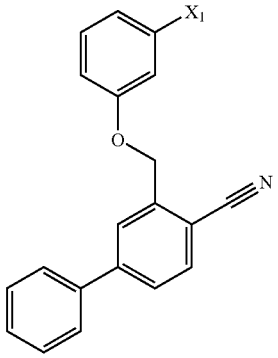 | 0.23 | NA | ND |
| 116 | 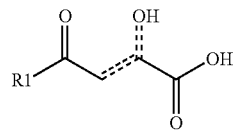 | 0.3 | NA | ND |
TABLE IXa-continued
most active HCV-inhibitors
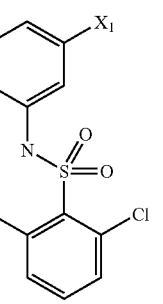
| Ex. No. | R1 | HCV | HIV | HBV |
|---|---|---|---|---|
| 120 | 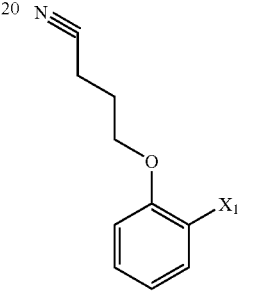 | 0.36 | 80 | ND |
| 20 | 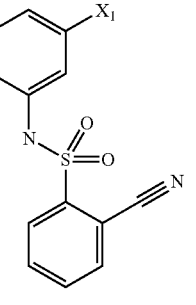 | 0.38 | 27 | ND |
| 72 | 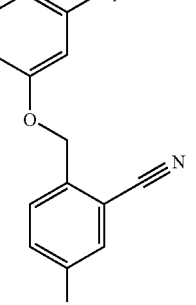 | 0.48 | NA | ND |
| 99 |  | 0.6 | 50 | ND |

TABLE IXa-continued most active HCV-inhibitors

R1–C(=O)–CH=C(OH)–C(=O)–OH

| Ex. No. | R1 | HCV | HIV | HBV |
|---|---|---|---|---|
| 78 | 3-(naphthalen-1-ylsulfonylamino)phenyl | 0.67 | 35 | ND |
| 88 | 3-(2,5-dichlorophenylsulfonylamino)phenyl | 0.7 | NA | ND |
| 84 | 3-((2-carboxythiophen-3-yl)methoxy)phenyl | 0.95 | NA | ND |
| 21 | 4-methyl-2-(3-cyanopropoxy)phenyl | 1 | >50 | ND |
| 23 | 3-hydroxyphenyl | 1 | 59 | ND |
| 112 | 3-((2-cyanophenoxy)methyl)phenyl | 1.33 | 90 | ND |
| 155 | 3-benzyloxy-5-hydroxyphenyl | 1.4 | 130 | 416 |
| 36 | 4-chloro-2-(3-cyanopropoxy)phenyl | 1.6 | 24 | ND |
| 90 | 3-((2-carboxyphenyl)methoxy)phenyl | 1.8 | NA | ND |
| 165 | 2,4-dimethylphenyl | 2 | NA | ND |
| 18 | 3-(2-phenylethoxy)phenyl | 2.2 | 30 | ND |

TABLE IXa-continued most active HCV-inhibitors $$\underset{R1}{\overset{O}{\underset{\|}{C}}}\diagup\hspace{-1em}\diagdown\underset{\underset{O}{\|}}{\overset{OH}{C}}\diagup OH$$

| Ex. No. | R1 | HCV | HIV | HBV |
|---|---|---|---|---|
| 161 | 4-methylphenyl (H₃C-C₆H₄-X₁) | 2.8 | 320 | 108 |
| 80 | 3-(N'-phenylureido)phenyl | 3 | NA | ND |
| 27 | HOOC-(CH₂)₃-O-(2-X₁-phenyl) | 3 | >50 | ND |
| 7 | 2,6-difluorobenzyloxy-3-X₁-phenyl | 3.3 | 61 | 6 |
| 16 | allyloxy-2-X₁-phenyl | 4.3 | >100 | ND |
| 162 | 4-hydroxyphenyl | 5.5 | NA | ND |
| 1 | phenyl | 5.6 | 90 | NA |
| 103 | 3-[(5-phenylisoxazol-3-yl)methoxy]phenyl | 6 | NA | ND |
| 243 | adamantyl | 6.7 | 26.8 | ND |
| 198 | 5-bromothien-2-yl | 7.9 | NA | ND |
| 4 | 3-benzyloxyphenyl | 8 | >100 | ND |
| 192 | 3,5-dimethylthien-2-yl | 8.2 | NA | ND |
| 66 | 3-(benzoylamino)phenyl | 11 | NA | ND |

TABLE IXa-continued most active HCV-inhibitors $$\text{R1}-\underset{O}{\overset{O}{\|}}-CH=C(OH)-COOH$$

| Ex. No. | R1 | HCV | HIV | HBV |
|---|---|---|---|---|
| 19 | 3-X₁-phenyl (methyl substituted) | 12 | 77 | ND |
| 179 | 1-(4-hydroxybenzyl)-pyrrol-2-yl-X₁ | 12.8 | NA | NA |
| 190 | 1-(4-fluorobenzyl)-4-iodo-pyrrol-2-yl-X₁ | 18 | NA | NA |
| 24 | HOOC-C(O)-NH-(3-X₁-phenyl) | 19 | 71 | ND |
| 49 | 3,5-dibromobenzyl-(3-X₁-phenyl) | 32 | NA | ND |

TABLE IXb most active HBV-Pol-inhibitors $$\text{R1}-\underset{O}{\overset{O}{\|}}-CH=C(OH)-COOH$$

| Ex. No. | R1 | HCV | HIV | HBV |
|---|---|---|---|---|
| 206 | 4-fluorobenzyl-thiophen-2-yl-X₁ | 65 | NA | 2 |

TABLE IXb-continued most active HBV-Pol-inhibitors $$\text{R1}-\underset{O}{\overset{O}{\|}}-CH=C(OH)-COOH$$

| Ex. No. | R1 | HCV | HIV | HBV |
|---|---|---|---|---|
| 205 | 3-fluorobenzyl-thiophen-2-yl-X₁ | 74 | NA | 3.3 |
| 225 | 5-phenyl-2-methyl-thiophen-3-yl-X₁ | 167 | 86 | 4 |
| 202 | benzyl-thiophen-2-yl-X₁ | 70 | >100 | 9 |
| 196 | 5-phenyl-thiophen-2-yl-X₁ | 15 | 50 | 9 |

TABLE IXc most active HIV-RT-inhibitors $$\text{R1}-\underset{O}{\overset{O}{\|}}-CH=C(OH)-COOH$$

| Ex. No. | R1 | HCV | HIV | HBV |
|---|---|---|---|---|
| 258 | 5-(3,5-dichlorophenyl)-furan-2-yl-X₁ | >100 | 3.6 | NA |
| 218 | 5-(3-chloro-4-fluorophenyl)-furan-2-yl-X₁ | 41.2 | 11.8 | 40 |
| 259 | 5-(3,5-bis-trifluoromethylphenyl)-furan-2-yl-X₁ | >100 | 16 | NA |

TABLE IXc-continued most active HIV-RT-inhibitors

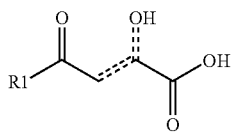

| Ex. No. | R1 | HCV | HIV | HBV |
|---|---|---|---|---|
| 40 | (2-X$_1$-phenyl)-CH$_2$-(4-F-phenyl) | 8.3 | 12 | NA |
| 20 | NC-(CH$_2$)$_3$-O-(2-X$_1$-phenyl) | 0.38 | 27 | ND |
| 8 | phenyl-CH$_2$-O-(2-X$_1$-phenyl) | 44 | 19 | ND |

2. Measurement of Inhibitory Activity

The effectiveness of the compounds set out above as polymerase inhibitors, stated above as IC$_{50}$ values, was assessed in screening assays as follows.

In initial tests, the compounds were tested to see if they were effective as inhibitors of the RNA-dependent RNA polymerase (RdRp) of hepatitis C virus (HCV). The HCV NS5B protein is the viral RdRp; compounds capable of interfering with the activity of this enzyme are thus expected to block viral replication.

Test for Inhibition of Hepatatis C Virus RdRp

WO96/37619 describes the production of recombinant HCV RdRp from insect cells infected with recombinant baculovirus encoding the enzyme. The purified enzyme was shown to possess in vitro RNA polymerase activity using RNA as template. The reference describes a polymerisation assay using poly (A) as a template and oligo (U) as a primer. Incorporation of tritiated UTP is quantified by measuring acid-insoluble radioactivity. The present inventors have employed this assay to screen the various compounds described above as inhibitors of HCV RdRp and other virally encoded polymerases.

Incorporation of radioactive UMP was measured as follows. The standard reaction (100 µl) was carried out in a buffer containing 20 mM tris/HCl pH 7.5, 5 mM MgCl$_2$, 1 mM DTT, 50 mM NaCl, 1 mM EDTA, 2 OU Rnasin (Promega), 0.05% Triton X-100, 1 µCi[$^3$H] UTP (40 Ci/mmol,NEN), 10 µM UTP and 10 µg/ml poly (A). Oligo (U)$_{12}$ (1 µg/ml, Genset) was added as a primer. The final NS5B enzyme concentration was 20 nM. After 1 hour incubation at 22° C. the reaction was stopped by adding 100 µl of 20% TCA and applying samples to DE81 filters. The filters were washed thoroughly with 5% TCA containing 1M Na$_2$HPO$_4$/NaH$_2$PO$_4$, pH 7.0, rinsed with water and then ethanol, air dried, and the filter-bound radioactivity was measured in the scintillation counter. By carrying out the reaction in the presence of various concentrations of each of the compounds set out above it was possible to determine IC50 values for each compound with the formula:

% residual activity=$100/(1+[I]/IC_{50})^s$ where [I] is the inhibitor concentration and "s" is the slope of the inhibition curve.

Test for Inhibition of Hepatitis B Virus Polymerase

Analogous assays employed the polymerase of hepatitis B virus (HBV pol), obtained in the form of viral particles from the sera of HBV positive patients. These particles contain a polymerase bound to an incomplete double stranded DNA template. In the assay the incorporation of $^{32}$P-dNTP is measured as radioactivity incorporated in acid insoluble precipitate.

The standard reaction (100 µl) was carried out in a buffer containing 50 mM tris/HCl pH 7.5, 30 mM MgCl 2 , 1 mM DTT, 100 mM KCl, 0.02% Triton X-100, 1 µCi[$^{32}$P] dCTP (300 Ci/mmol, NEN), 1 µM dATP, dTTP, dGTP. After 1 hour incubation at 37° C. the reaction was stopped by adding 100 µl of 20% TCA and applying samples to DE81 filters. The filters were processed and IC$_{50}$ values calculated as described above.

Test for Inhibition of Human Immunodeficiency Virus-1 Reverse Transcriptase

Analogous assays employed the reverse transcriptase of HIV (HIV -1RT) from Boehringer Mannhium.

Incorporation of radioactive dTTP was measured as follows. The standard reaction (100 µl) was carried out in a buffer containing 50 mM tris/HCl pH 8.2, 2.5 mM MgCl 2 , 1 mM DTT, 80 mM KCl, 5 mM EGTA, 0.05% Triton X-100, 1 µCi[3H] dTTP (40 Ci/mmol, NEN), 10 µM UTP and 10 µg/ml poly(A)/dT (from Pharmacia). The final HIV-1RT (enzyme concentration was 1 nM. After 1 hour incubation at 37° C. the reaction was stopped by adding 100 µl of 20% TCA and applying samples to DE81 filters. The filters were processed and IC$_{50}$ values calculated as described above.

The results demonstrate that the compounds of the present invention are effective as inhibitors of viral polymerases at low micromolar concentrations.

It is apparent from the tables above that a compound of the present invention which is effective in the inhibition of one of the RNA dependent polymerases tested may not necessarily be as effective in inhibiting the other RNA dependent polymerases. The results shown in the tables above indicate a general trend, although this is not without exception. Generally, the most active inhibitors of HCV RdRp contained a phenyl ring attached to the diketoacid, whereas the HIV-RT inhibitors contained a furanyl group and those of HBV polymerase a thiophene group.

While not wishing to be bound by any particular theory, the present inventors hypothesize that the diketoacid fragment of the compounds of the present invention inhibits RNA dependent polymerase activity by providing an "active site anchor" and interacting with divalent metal cations (Mg$^{2+}$, Mn$^{2+}$) required for polymerase activity. The ring system found on the left hand side of the molecule can apparently be modified in order to build specificity towards a given polymerase.

The invention claimed is:

1. A compound, or a pharmaceutically acceptable ester or salt thereof, of formula:

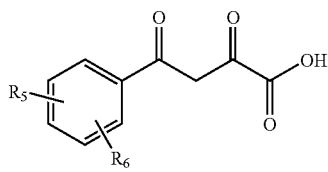

wherein $R_5$ is selected from the following substituent groups:
(1) an alkyl group having 1 to 12 carbon atoms, substituted by —CN and optionally interrupted by a group selected from —O—, —S—, —NR$_3$—, —C(=O)—, —CO$_2$—, —OCO—, —CONR$_3$—, —NR$_3$CONR$_3$—, —SO$_2$—, —NR$_3$SO$_2$—, and —SO$_2$NR$_3$—; where each $R_3$ independently is H or lower alkyl of 1 to 6 carbon atoms;
(2) —OR$_4$ where $R_4$ is an aralkyl group having 3 to 16 carbon atoms optionally substituted with any one or more of groups:
  (a) —OH;
  (b) —SH;
  (c) -halogen,
  (d) —CO$_2$H;
  (e) —CN;
  (f) —NO$_2$;
  (g) —NR$_1$R$_2$ wherein each of $R_1$ and $R_2$ is selected from H and lower alkyl groups having 1 to 6 carbon atoms;
  (h) —SO$_2$NR$_1$R$_2$ where $R_1$ and $R_2$ are as defined above;
  (i) —CONR$_1$R$_2$, —NR$_1$CO$_2$H, or —NR$_1$COCOOH where $R_1$ and $R_2$ are as defined above;
  (j) an alkyl (or alkenyl or alkynyl group) group having 1 to 12 carbon atoms, optionally substituted by any one or more of the groups (a)–(i) above and/or optionally interrupted by a group selected from —O—, —S—, —NR$_3$—, —C(=O)—, —CO$_2$—, —OCO—, —CONR$_3$—, —NR$_3$CONR$_3$—, —SO$_2$—, —NR$_3$SO$_2$—, and —SO$_2$NR$_3$—; where each $R_3$ independently is as defined above; and
(3) —NHSO$_2$R$_4$* or —SO$_2$NHR$_4$*, where R$_4$* is an aryl group having 2 to 10 carbon atoms optionally substituted with any one or more of groups (a) to (j) above; and
wherein $R_6$ is independently selected from hydrogen and the substituent groups (a) to (j) as defined above.

2. The compound, salt or ester according to claim 1, wherein $R_5$ is an alkyl group having 1 to 7 carbon atoms substituted by —CN and interrupted by the group —O—.

3. The compound, salt or ester according to claim 2, wherein $R_5$ is —O(CH$_2$)$_3$CN.

4. The compound, salt or ester according to claim 3, wherein $R_5$ is —O(CH$_2$)$_3$CN at the 2-position of the phenyl ring; and $R_6$ is H, OH, methyl, chloro, bromo, or —NH$_2$.

5. The compound, salt or ester according to claim 4, wherein $R_6$ is at the 4- or 5-position of the phenyl ring.

6. The compound, salt or ester according to claim 1, wherein $R_5$ is —OCH$_2$Ar wherein Ar is an optionally substituted aryl group.

7. The compound, salt or ester according to claim 6, wherein $R_6$ is H or OH.

8. The compound, salt or ester according to claim 6, wherein Ar is an optionally substituted phenyl group.

9. The compound, salt or ester according to claim 8, wherein Ar is phenyl optionally substituted with one or more groups selected from halogen, —CN, —CO$_2$H, —CF$_3$, and ether.

10. The compound, salt or ester according to claim 6, wherein $R_5$ is at a position on the phenyl ring that is meta to the diketoacid group.

11. The compound, salt or ester according to claim 10, wherein wherein Ar is optionally substituted phenyl.

12. The compound, salt or ester according to claim 11, wherein $R_6$ is H.

13. The compound, salt or ester according to claim 1, wherein $R_5$ is —NHSO$_2$Ar wherein Ar is an optionally substituted aryl group.

14. The compound, salt or ester according to claim 13, wherein Ar is an optionally substituted phenyl group.

15. The compound, salt or ester according to claim 13, wherein Ar is aryl optionally substituted with one or more groups selected from —CN, halogen, —CF$_3$, C$_{1-6}$ alkyl, hydroxy, ether, and —NO$_2$.

16. The compound, salt or ester according to claim 13, wherein $R_5$ is at a position on the phenyl ring that is meta to the diketoacid group.

17. The compound, salt or ester according to claim 16, wherein Ar is optionally substituted phenyl.

18. The compound, salt or ester according to claim 17, wherein $R_6$ is H.

19. A pharmaceutical composition comprising a compound, salt or ester of claim 1 in combination with a pharmaceutically acceptable excipient, diluent or carrier.

20. A compound selected from the group consisting of:

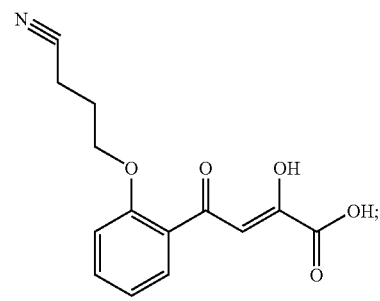

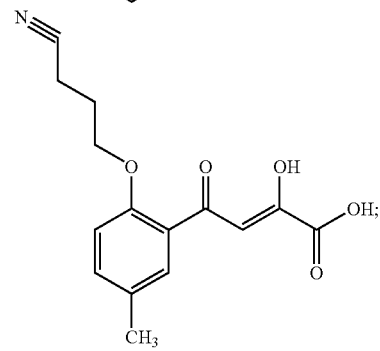

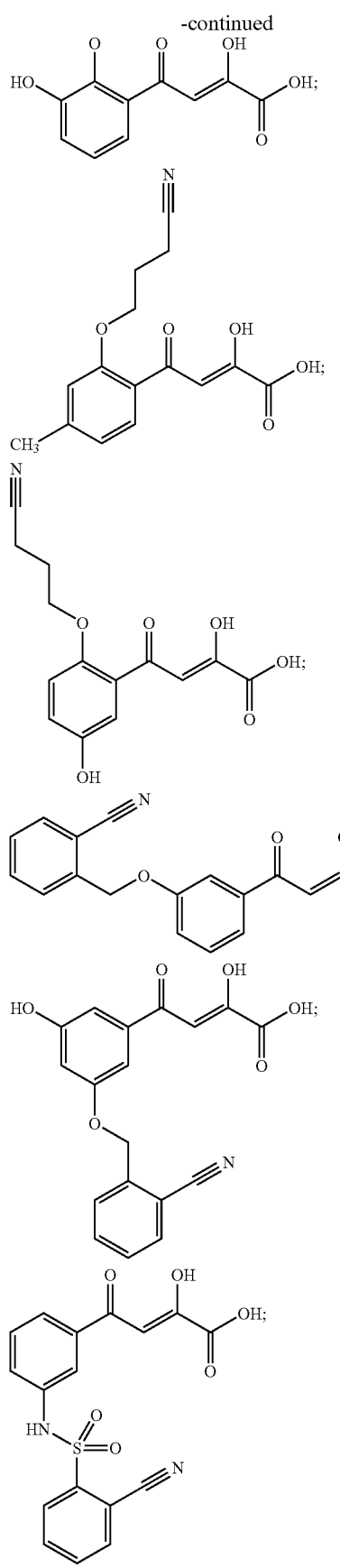
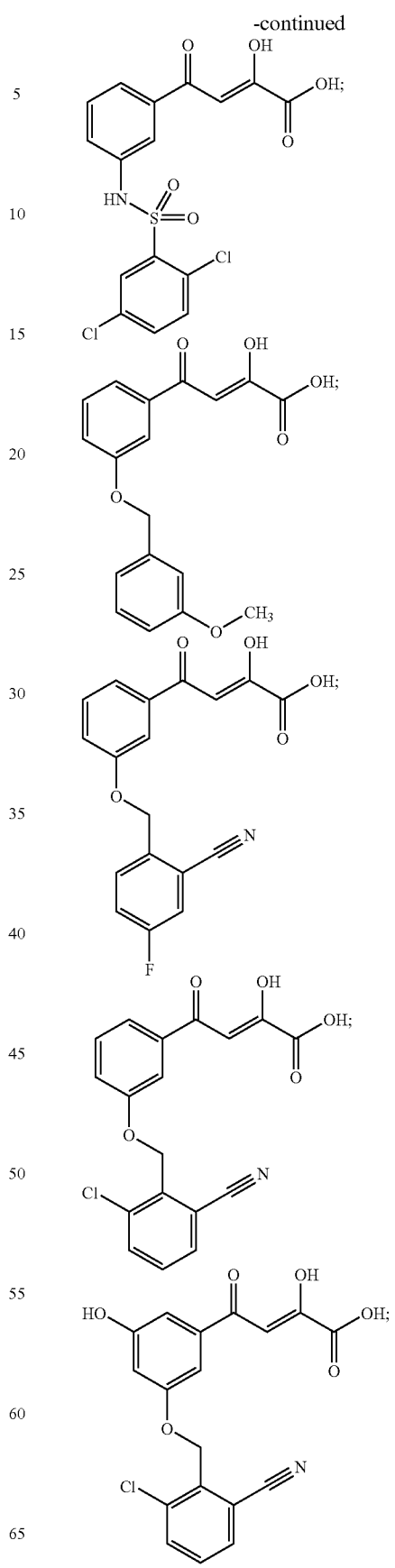

-continued
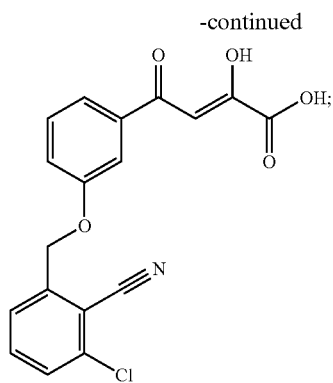
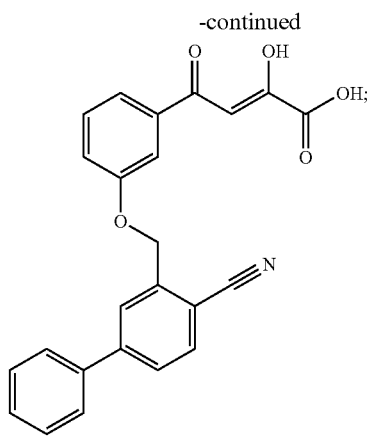
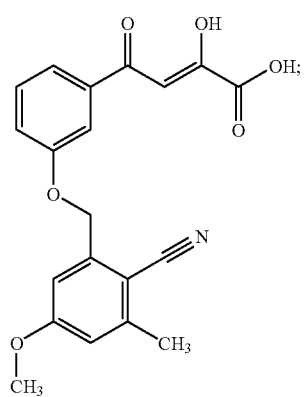
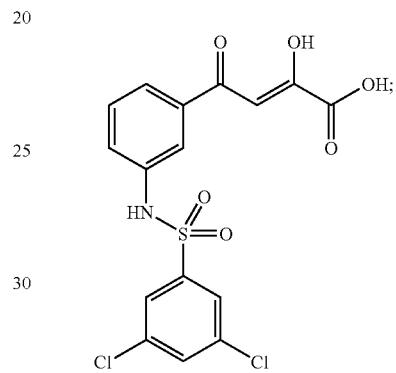
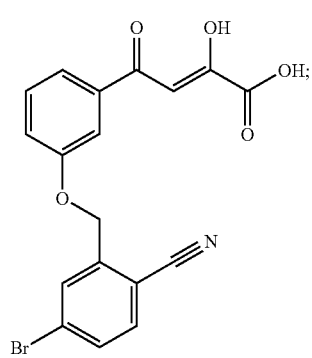
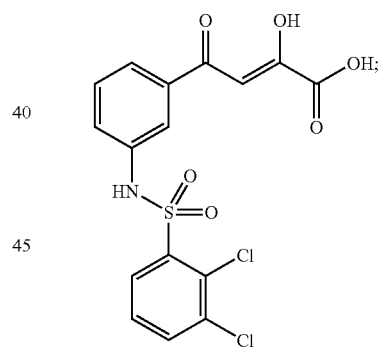
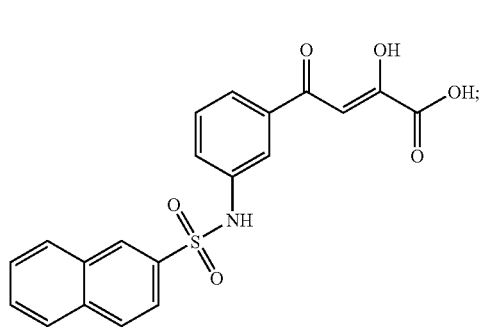
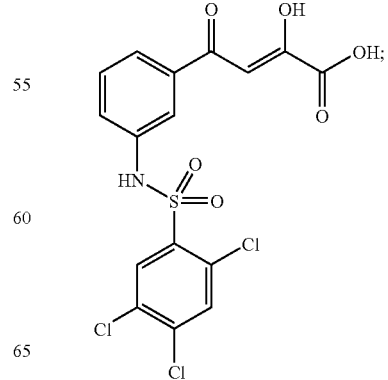

-continued
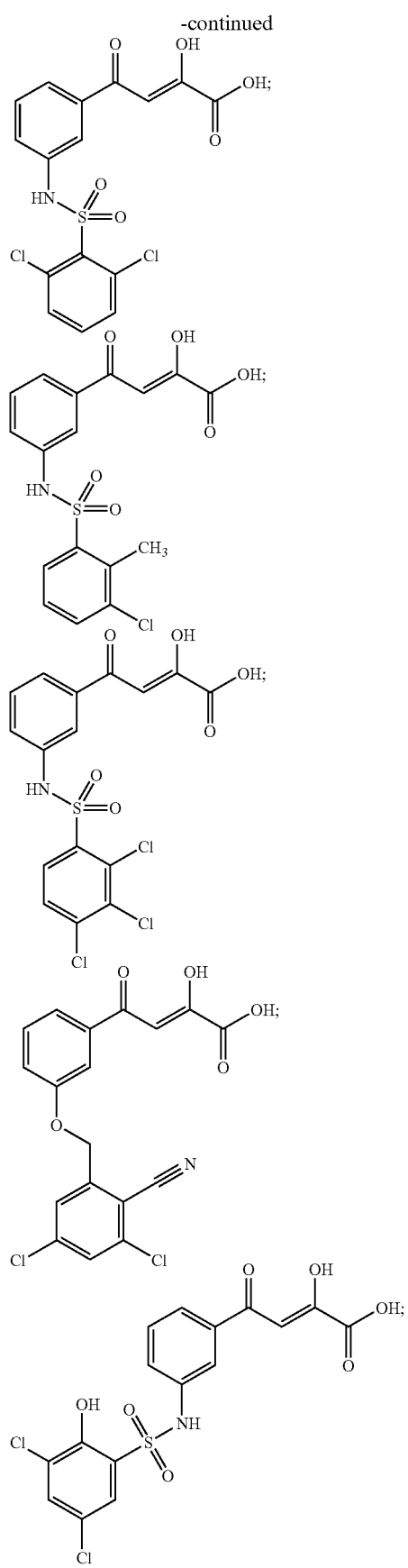
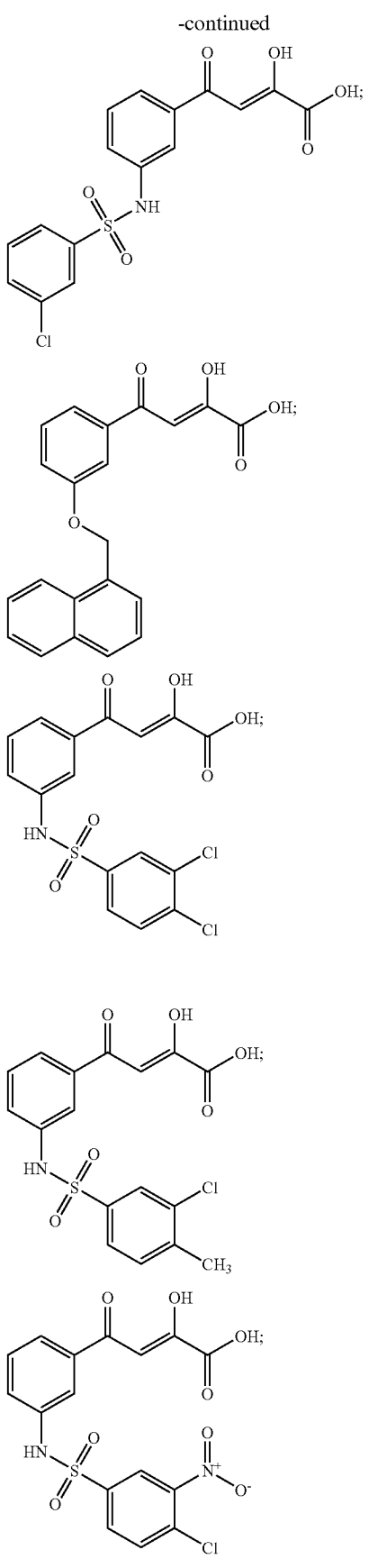

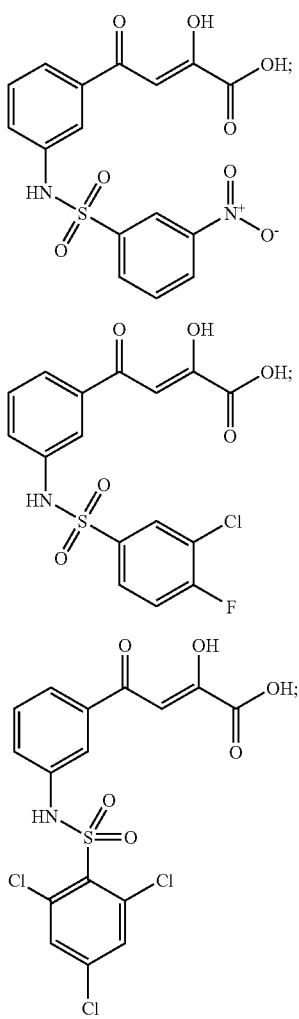
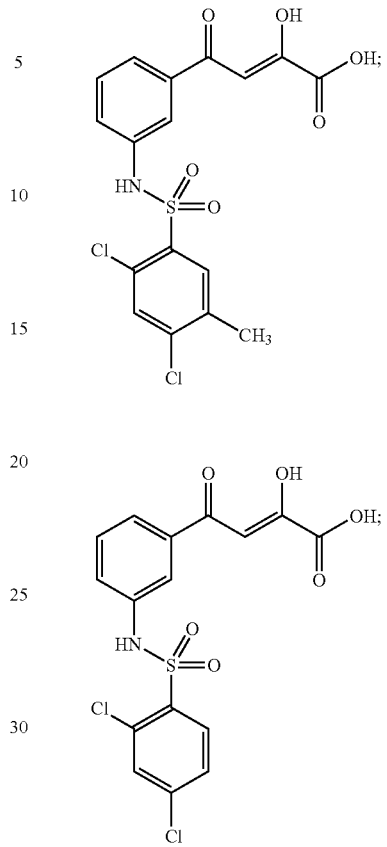
and pharmaceutically acceptable salts and esters thereof.
* * * * *